(12) United States Patent
Blanchard

(10) Patent No.: US 9,369,792 B2
(45) Date of Patent: Jun. 14, 2016

(54) ROUND VARIABLE WALL EARBUD

(71) Applicant: Klipsch Group, Inc., Indianapolis, IN (US)

(72) Inventor: Mark A. Blanchard, Lebanon, IN (US)

(73) Assignee: Klipsch Group, Inc., Indianapolis, IN (US)

( * ) Notice: Subject to any disclaimer, the term of this patent is extended or adjusted under 35 U.S.C. 154(b) by 179 days.

(21) Appl. No.: 13/966,780

(22) Filed: Aug. 14, 2013

(65) Prior Publication Data

US 2015/0047650 A1 Feb. 19, 2015

(51) Int. Cl.
*H04R 1/10* (2006.01)
*H04R 25/00* (2006.01)
*A61F 11/08* (2006.01)

(52) U.S. Cl.
CPC ............ *H04R 1/1016* (2013.01); *H04R 25/652* (2013.01); *A61F 2011/085* (2013.01)

(58) Field of Classification Search
CPC combination set(s) only.
See application file for complete search history.

(56) References Cited

U.S. PATENT DOCUMENTS

| | | |
|---|---|---|
| 177,253 A | 5/1876 | Keats |
| 789,876 A | 5/1905 | Pape |
| 1,556,775 A | 10/1925 | Fensky |
| 2,246,737 A | 6/1941 | Knudsen |
| 2,430,229 A | 11/1947 | Kelsey |
| 2,487,038 A | 11/1949 | Baum |
| 2,521,414 A | 9/1950 | Schier |
| 2,719,523 A | 10/1955 | Von Glerke |
| 2,987,584 A | 6/1961 | Webber |
| 3,061,689 A | 10/1962 | McCarrell et al. |
| 3,080,011 A | 3/1963 | Henderson |
| D207,216 S | 3/1967 | Geib |
| RE26,258 E | 8/1967 | Martin |
| 3,414,685 A | 12/1968 | Geib et al. |
| 3,415,246 A | 12/1968 | Hill |
| 3,548,118 A | 12/1970 | Hutchings |
| 3,610,841 A | 10/1971 | Hutchings |
| 3,618,697 A | 11/1971 | Littmann |
| 3,692,958 A | 9/1972 | Dymoke |
| 3,865,998 A | 2/1975 | Weiss et al. |
| 3,993,879 A | 11/1976 | Larkin |
| 4,006,321 A | 2/1977 | Carlson |
| D245,202 S | 7/1977 | Asker |
| 4,039,765 A | 8/1977 | Tichy et al. |
| 4,122,841 A | 10/1978 | Rock et al. |
| 4,261,432 A | 4/1981 | Gunterman |

(Continued)

FOREIGN PATENT DOCUMENTS

| | | |
|---|---|---|
| EP | 0959773 B1 | 12/2003 |
| EP | 1578168 A3 | 9/2005 |

(Continued)

*Primary Examiner* — Ophelia A Hawthorne
(74) *Attorney, Agent, or Firm* — Indiano & McConnell LLP

(57) ABSTRACT

An ear tip is disclosed that comprises an annular flange having a first end tapering downwardly to a second end and having a circular lateral cross-section. The annular flange is defined by a plurality of sections and each section has a varying wall thickness. An inner body extends internally from the first end within a hollow interior defined by the annular flange toward the second end. An acoustic channel extends through the inner body, where the annular flange at least partially occludes an ear canal from ambient noise and creates at least a partial air seal in the ear canal and the acoustic channel is configured to allow the passage of sound into the ear canal when the inner body is connected with a sound source.

10 Claims, 2 Drawing Sheets

(56) References Cited

U.S. PATENT DOCUMENTS

| | | | |
|---|---|---|---|
| D259,279 S | 5/1981 | Takeda | |
| 4,325,453 A | 4/1982 | Moussette | |
| 4,335,281 A | 6/1982 | Scott et al. | |
| 4,347,911 A | 9/1982 | Bertagna et al. | |
| 4,548,082 A | 10/1985 | Engebretson et al. | |
| 4,677,675 A | 6/1987 | Killion et al. | |
| 4,764,168 A | 8/1988 | Suh | |
| D298,356 S | 11/1988 | Falco | |
| 4,867,149 A | 9/1989 | Falco | |
| 4,870,688 A | 9/1989 | Voroba et al. | |
| 4,875,233 A | 10/1989 | Derhaag et al. | |
| 4,913,259 A | 4/1990 | Packard | |
| 4,936,411 A | 6/1990 | Leonard | |
| 5,031,219 A | 7/1991 | Ward et al. | |
| D330,761 S | 11/1992 | Falco | |
| 5,188,123 A | 2/1993 | Gardner, Jr. | |
| 5,201,007 A | 4/1993 | Ward et al. | |
| 5,288,953 A | 2/1994 | Peart | |
| 5,295,193 A | 3/1994 | Ono | |
| 5,298,692 A | 3/1994 | Ikeda et al. | |
| D353,379 S | 12/1994 | Nakamura et al. | |
| 5,487,012 A | 1/1996 | Topholm et al. | |
| 5,692,059 A | 11/1997 | Kruger | |
| 5,712,453 A | 1/1998 | Bungardt et al. | |
| 5,781,638 A | 7/1998 | Hosaka et al. | |
| 5,824,968 A | 10/1998 | Packard et al. | |
| D402,752 S | 12/1998 | Falco | |
| 5,917,918 A | 6/1999 | Callahan | |
| 5,957,136 A | 9/1999 | Magidson et al. | |
| 5,979,589 A | 11/1999 | Aceti | |
| D427,304 S | 6/2000 | Magidson et al. | |
| 6,175,633 B1 | 1/2001 | Morrill et al. | |
| 6,205,227 B1 | 3/2001 | Mahoney et al. | |
| 6,253,871 B1 | 7/2001 | Aceti | |
| 6,258,043 B1 | 7/2001 | Raviv et al. | |
| 6,359,993 B2 | 3/2002 | Brimhall | |
| 6,386,314 B1 * | 5/2002 | Sheehan | A61B 5/12 181/129 |
| D468,299 S | 1/2003 | Boesen | |
| D468,721 S | 1/2003 | Nguyen | |
| 6,513,621 B1 | 2/2003 | Destauriers et al. | |
| 6,532,295 B1 | 3/2003 | Brimhall et al. | |
| D473,652 S | 4/2003 | Darley et al. | |
| 6,574,345 B1 | 6/2003 | Huang | |
| 6,643,378 B2 | 11/2003 | Schumaier | |
| 6,648,813 B2 | 11/2003 | Zilberman et al. | |
| 6,688,421 B2 | 2/2004 | Dyer et al. | |
| 6,695,093 B1 | 2/2004 | Falco | |
| 6,751,327 B1 | 6/2004 | Urso et al. | |
| D499,397 S | 12/2004 | Hlas et al. | |
| 6,920,228 B2 | 7/2005 | Redmer et al. | |
| 6,920,229 B2 | 7/2005 | Boesen | |
| 6,940,988 B1 | 9/2005 | Shennib et al. | |
| D517,054 S | 3/2006 | Yang | |
| 7,010,137 B1 | 3/2006 | Leedom et al. | |
| 7,072,476 B2 | 7/2006 | White et al. | |
| 7,079,662 B2 | 7/2006 | Niederdränk | |
| 7,082,206 B2 | 7/2006 | Mahoney et al. | |
| 7,092,543 B1 | 8/2006 | Mahoney et al. | |
| 7,107,993 B2 | 9/2006 | Magidson | |
| 7,123,733 B1 | 10/2006 | Borowsky et al. | |
| D535,644 S | 1/2007 | Drambarean et al. | |
| 7,185,655 B1 * | 3/2007 | Redon | 128/864 |
| D542,773 S | 5/2007 | Drambarean et al. | |
| 7,221,768 B2 | 5/2007 | Sjursen et al. | |
| D549,222 S | 8/2007 | Huang | |
| D550,201 S | 9/2007 | Drambarean et al. | |
| D550,567 S | 9/2007 | Söderström et al. | |
| D550,655 S | 9/2007 | Falco | |
| 7,314,047 B2 | 1/2008 | Falco | |
| D563,945 S | 3/2008 | Johns et al. | |
| D565,022 S | 3/2008 | Belliveau et al. | |
| D567,217 S | 4/2008 | Kamo et al. | |
| D569,842 S | 5/2008 | Yang | |
| D575,767 S | 8/2008 | Lee | |
| D575,773 S | 8/2008 | Yanai | |
| D579,006 S | 10/2008 | Kim et al. | |
| 8,573,353 B2 * | 11/2013 | Mulvey | A61F 11/08 181/130 |
| 2002/0058881 A1 | 5/2002 | Raviv et al. | |
| 2002/0076057 A1 | 6/2002 | Voix | |
| 2003/0159878 A1 | 8/2003 | Hakansson et al. | |
| 2003/0172938 A1 | 9/2003 | Falco | |
| 2004/0047481 A1 | 3/2004 | Bauman | |
| 2004/0240691 A1 | 12/2004 | Grafenberg | |
| 2005/0018838 A1 | 1/2005 | Meunier et al. | |
| 2005/0111687 A1 | 5/2005 | Lederer | |
| 2005/0165460 A1 | 7/2005 | Erfan | |
| 2006/0050912 A1 | 3/2006 | Kidd et al. | |
| 2006/0050916 A1 | 3/2006 | Wehner | |
| 2006/0147072 A1 | 7/2006 | Sodoma et al. | |
| 2006/0159297 A1 | 7/2006 | Wirola et al. | |
| 2008/0187159 A1 | 8/2008 | Blanchard | |
| 2011/0268308 A1 * | 11/2011 | Vasquez | 381/380 |

FOREIGN PATENT DOCUMENTS

| | | |
|---|---|---|
| EP | 1681904 A1 | 7/2006 |
| JP | 10023578 A | 1/1998 |
| JP | 2000210327 A | 8/2000 |
| WO | 9737593 A1 | 10/1997 |
| WO | 9904601 A1 | 1/1999 |
| WO | 0108443 A2 | 2/2001 |
| WO | 2004077924 A2 | 9/2004 |
| WO | 2005025268 A1 | 3/2005 |
| WO | 2005112503 A1 | 11/2005 |
| WO | 2006068772 A2 | 6/2006 |

* cited by examiner

ROUND VARIABLE WALL EARBUD

INTRODUCTION

The inventions disclosed and claimed herein are earbuds that come in contact with the ear canal wall, adapted for use with earphones, stethoscopes, perytympanic hearing instruments, headsets, and ear plugs for hearing protection, and more particularly "in ear" applications. The devices to which the ear tips can be operatively attached are generally known in the art, including earphones that can be positioned on the head or over the ear, in the ear and wires capable of operatively connecting the ear tip to an audio source such as an analog or digital audio player. Alternative uses include operative attachment to stethoscopes, hearing aids, headsets, and as ear plugs.

DETAILED DESCRIPTION OF REPRESENTATIVE EMBODIMENTS

Figure 1:
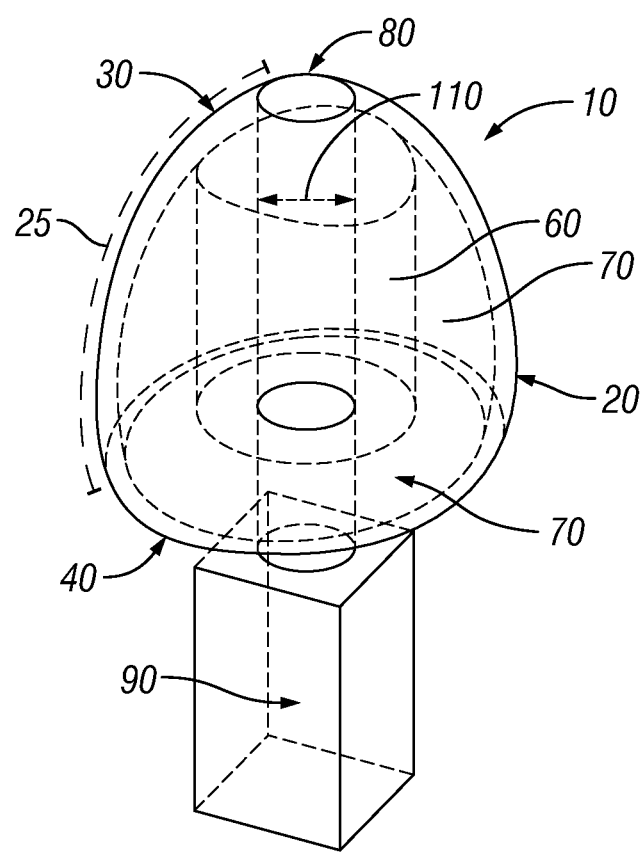
FIG. 1 shows a perspective view of one embodiment of an earbud.

For the purpose of promoting an understanding of the principles of the invention, reference is now made to the embodiments illustrated in the drawings and specific language is used to describe the same. No limitation of the scope of the invention is intended. Alterations and modifications to the illustrated devices, and other applications of the principles of the invention as illustrated herein are contemplated as would normally occur to one skilled in the art to which the invention relates.

Figure 2:
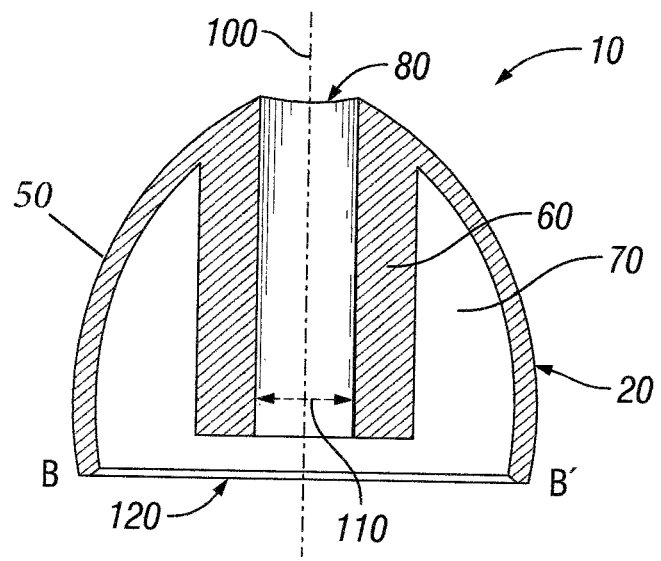
FIG. 2. shows a longitudinal cross-section of the earbud shown in FIG. 1.

As shown in FIGS. 1 and 2, the earbud 10 has an annular flange 20 having a first or upper end 30, a second or lower end 40, and a circular cross section 50 (shown for example in FIG. 2). An inner body 60 extends from the first end 30 toward the second end 40 within a chamber 70 defined by the annular flange 20. An acoustic channel 80 extends through the inner body 60 to connect operatively the sound source or transducer 90 to the ear drum (not shown).

An inner body 60 is formed as part of the flange 20. The inner body 60 is positioned so that its longitudinal axis is generally concentric with the longitudinal axis of the flange 20 (i.e. along axis 100 as shown on FIG. 2). The acoustic channel 80 extends through the inner body 60 and the first end 30. A transducer (not shown) may be positioned within the chamber 70 such that a portion of the transducer 90 is positioned within the acoustic channel 80 defined by the inner body 60. The inner body 60 may be formed integrally with the flange 20 or as a separate piece which is then attached to the flange 20.

The inner diameter 110 of the acoustic channel 80 is sized to secure an acoustic connection from a sound source or transducer 90. The acoustic channel 80 in one version has a diameter of about 1.26 millimeters. In another version, the acoustic channel 80 has a diameter of about 1.40 millimeters. Variations to the diameter of the acoustic channel 80 can be made without varying from the scope of the invention disclosed and claimed herein.

The exterior surface 25 of the flange 20 tapers upwardly from the second end 40 to the first end 30. The arc of the taper can be constant or variable. In one version the radius is 5 millimeters. In another version, the radius is 9 millimeters. In other embodiments, the flange 20 has a generally circular three-dimensional shape. Again, variations in the arc or radius of the taper can be made without varying from the scope of the invention disclosed and claimed herein.

Referring to FIG. 2, the earbud 10 has an axis 120 along B-B'. The axis 120 has a length from about 9 millimeters to about 15 millimeters. The length of the axis 120 can be varied without departing from the scope of the inventions disclosed and claimed herein.

Figure 3:
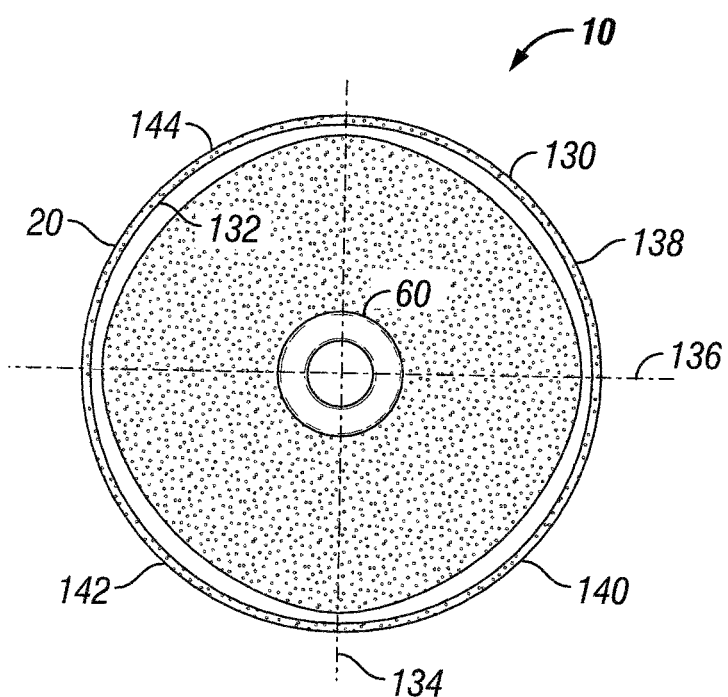
FIG. 3 shows a bottom view of the earbud shown in FIG. 1.

Referring to FIG. 3, a bottom view of the earbud 10 is illustrated. In one form, an outer surface 130 of the annular flange 20 has a generally circular shape. An inner surface 132 of the annular flange 20 varies in shape as the thickness of the annular flange 20 varies. A horizontal axis 136 and a vertical axis 134 are illustrated and as the annular flange 20 tapers towards each of these axes 134, 136 the thickness of the annular flange 20 decreases. At portions 138, 140, 142, and 144, which is at about 45°, 135°, 225°, and 315° respectively, the annular flange 20 is thicker than at the intersections of each axes 134, 136. As such, moving around the circumference of the flange 20 the thickness of the flange or wall 20 transitions from a larger thickness to a smaller thickness.

In the form illustrated in FIG. 3, the annular flange 20 is divided into four quadrants or sections 138, 140, 142, 144. Each respective quadrant or section includes a portion of the annular flange 20 that has a varying wall thickness. The annular flange 20 varies from thick to thin as it passes through each quadrant. Although four quadrants 138, 140, 142, 144 are illustrated in FIG. 3, it should be appreciated that the circular shape of the earbud 10 could be divided up into any number of quadrants or sections such as, by way of example, two quadrants, three quadrants, five quadrants, and so forth. In each form, the thickness of the annular flange 20 will vary from thick to thin as it passes through each quadrant. In the form illustrated in FIG. 3, the flange 20 varies from about 480 micrometers at its thickest part to about 179 micrometers at its thinnest part.

Rigid, deformable, flexible, elastic or resilient materials provide flexibility in sizing the earbud, comfort, audio quality and durability. In one embodiment, the flange 20 is a polymer. In another embodiment, the flange 20 is an elastomeric polymer.

While the use of words such as preferable, preferably, preferred or more preferred utilized in the description indicate that the feature so described may be more desirable, such feature(s) may not be necessary. Embodiments lacking the same are within the scope of the invention as defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

I claim:

1. An ear tip, comprising:
   an annular flange having an upper end and a lower end, wherein said flange has a circular lateral cross section running from approximately the upper end to the lower end, wherein said flange varies in thickness from a larger thickness to a smaller thickness around a circumference of said flange along said circular lateral cross section running from approximately the upper end to the lower end, wherein said flange varies in thickness in four sections such that said flange is at said smaller thickness at an intersection with a horizontal axis and a vertical axis of said flange and is at said larger thickness at the middle of each of said four sections between said horizontal axis and said vertical axis, an inner body extending internally from the first end within a hollow interior defined by the flange toward the second end, and an acoustic channel extending through the inner body, where the flange at least partially occludes an ear canal from ambient noise and creates at least a partial air seal in the ear canal and the acoustic channel is configured to allow the passage of sound into the ear canal when the inner body is connected with a sound source.

2. The ear tip of claim 1 wherein said flange tapers to the lower end from the upper end.

3. The ear tip of claim 1 wherein said larger thickness is about 480 micrometers.

4. The ear tip of claim 1 wherein said smaller thickness is about 179 micrometers.

5. The ear tip of claim 1 wherein the flange comprises a flexible material.

6. The ear tip of claim 1 wherein the flange comprises a deformable material.

7. The ear tip of claim 1 wherein the flange comprises an elastic material.

8. The ear tip of claim 1 wherein the flange comprises a resilient material.

9. An ear tip, comprising:
an annular flange having a first end tapering downwardly to a second end and having a circular lateral cross-section, wherein said annular flange is defined by a first section, a second section, a third section, and a fourth section, wherein said first, second third, and fourth section that are located between a vertical axis and a horizontal axis, wherein each said section has a varying wall thickness, wherein the varying wall thickness is defined by a thicker wall portion toward a central portion of each section and a thinner wall portion toward ends of each section where each section meets another section at the vertical axis and the horizontal axis, wherein said varying wall thickness runs from said first end to said second end, an inner body extending internally from the first end within a hollow interior defined by the annular flange toward the second end, and an acoustic channel extending through the inner body, where the annular flange at least partially occludes an ear canal from ambient noise and creates at least a partial air seal in the ear canal and the acoustic channel is configured to allow the passage of sound into the ear canal when the inner body is connected with a sound source.

10. The ear tip of claim 9 wherein said varying wall thickness varies from about 480 micrometers to about 179 micrometers.

* * * * *